United States Patent [19]

Eng

[11] Patent Number: 5,424,286
[45] Date of Patent: Jun. 13, 1995

[54] EXENDIN-3 AND EXENDIN-4 POLYPEPTIDES, AND PHARMACEUTICAL COMPOSITIONS COMPRISING SAME

[76] Inventor: John Eng, 5427 Arlington Ave., Bronx, N.Y. 10471

[21] Appl. No.: 66,480

[22] Filed: May 24, 1993

[51] Int. Cl.⁶ .................. A61K 38/16; C07K 14/46; C12N 15/63
[52] U.S. Cl. ........................ 514/2; 514/866; 435/69.1; 530/324
[58] Field of Search ............ 514/2, 866; 424/88; 435/69.1; 530/324

[56] References Cited

PUBLICATIONS

Schmidt et al. 1985. Diabetologia 28:704–707.
J. Eng & C. Eng, Exendin-3 and -4 are Insulin Secretagogues; Regulatory Peptides 40: 142 (1992).
Eng, J. et al., Purification and Structure of Exendin-3, a New Pancreatic Secretagogue Isolated from *Heloderma horridum* Venom; J. Biol. Chem. 265:20259 (1990).
Raufman, J. -P., Exendin-3 a Novel Peptide from *Heloderma horridum* Venom, Interacts with Vasoactive Intestinal Peptide Receptors and a Newly Described Receptor on Dispersed Acini from Guinea Pig Pancreas; J. Biol. Chem. 266:2897 (1991).
Eng, J. et al., Isolation and Characterization of Exendin-4, an Exendin-3 Analogue, from *Heloderma suspectum* Venom; J. Biol. Chem. 267:7402 (1992).
Raufmann, J. -P., et al., Truncated Glucagon–like–Peptide–1 Interacts with Exendin Receptors on Dispersed Acini from Guinea Pig Pancreas; J. Biol. Chem. 267:21432 (1992).
John Eng, Exendin Peptides; The Mt. Sinai J. of Med. 59: 147 (1992).
Gutniak, M. et al., Antidiabetogenic Effect of Glucagon–Like Peptide–1 (7–36) Amide in Normal Subjects and Patients with Diabetes Mellitus; The New England J. Med. 326:1316 (1992).

*Primary Examiner*—Garnette D. Draper
*Assistant Examiner*—Elizabeth C. Kemmerer
*Attorney, Agent, or Firm*—Allegretti & Witcoff, Ltd.

[57] ABSTRACT

This invention encompasses pharmaceutical compositions containing exendin-3 or exendin-4, fragments thereof, or any combination thereof, and methods for the treatment of diabetes mellitus and the prevention of hyperglycemia.

7 Claims, 9 Drawing Sheets

EXENDIN-3 AND EXENDIN-4 POLYPEPTIDES, AND PHARMACEUTICAL COMPOSITIONS COMPRISING SAME

LICENSE RIGHTS

This U.S. Government has a paid-up license in this invention and the right in limited circumstances to require the patent owner to license others on reasonable terms as provided for by the terms of the agreement with the Department of Veterans Affairs, reference number 024I, GPB No. 20-560.

BACKGROUND OF THE INVENTION

1. Field of the Invention

This invention is in the field of the prevention and treatment of diabetes mellitus.

2. Description of the Prior Art

Diabetes mellitus (DM) is a major chronic illness found in humans with many consequences. Some complications arising from long-standing diabetes are blindness, kidney failure, and limb amputations. Insulin-dependent diabetes mellitus (IDDM) accounts for 10 to 15% of all cases of diabetes mellitus. The action of IDDM is to cause hyperglycemia (elevated blood glucose concentration) and a tendency towards diabetic ketoacidosis (DKA). Currently treatment requires chronic administration of insulin. Non-insulin dependent diabetes mellitus (NIDDM) is marked by hyperglycemia that is not linked with DKA. Sporadic or persistent incidence of hyperglycemia can be controlled by administering insulin. Uncontrolled hyperglycemia can damage the cells of the pancreas which produce insulin (the $\beta$-islet cells) and in the long term create greater insulin deficiencies. Currently, oral sulfonylureas and insulin are the only two therapeutic agents available in the United States. for treatment of Diabetes mellitus. Both agents have the potential for producing hypoglycemia as a side effect, reducing the blood glucose concentration to dangerous levels. There is no generally applicable and consistently effective means of maintaining an essentially normal fluctuation in glucose levels in DM. The resultant treatment attempts to minimize the risks of hypoglycemia while keeping the glucose levels below a target value. The drug regimen is combined with control of dietary intake of carbohydrates to keep glucose levels in control.

A fragment of human peptide molecule called, glucagon-like peptide-1 (GLP-1) has been found to be a glucose-dependent insulinotropic agent (Gutniak, M., et al. N. Engl. J. Bled. 1992; 326:1316–1322). GLP-1 is itself a fragment of the human proglucagon molecule. Another active fragment, glucagon-like insulinotropic peptide (GLIP), corresponds to GLP-1(7-36). It was reasoned that since GLIP is the naturally active form found in humans after a meal, this peptide may aid in glucose regulation in IDDM and NIDDM.

In normal subjects, the infusion of GLIP significantly lowered the meal-related increases in blood glucose concentration, and the plasma concentrations of insulin and glucagon. In patients with NIDDM, the treatment reduced the requirement for insulin by 8 fold. In patients with IDDM, the GLIP treatment lowered the insulin required by one half. This glucose-dependent activity is a very desirable characteristic for a therapeutic agent that can be used to treat DM avoiding tile complications of hypoglycemic side effects.

In 1981, it was discovered that Gila monster (Heloderma suspectum) venom stimulated pancreatic enzyme secretion in vitro (Raufman, J. P., et al., *Gastroenterology* 80:1257 abst. (1981); Raufman, J. P., et al., *Am. J. Physiol.* 242: G470-G474 (1982)). Several peptides have been isolated from the venom that can stimulate increased cAMP and amylase release from dispersed pancreatic acinar cells. These structural analogs to the mammalian peptides VIP (vasoactive intestinal peptide) and secretin include helospectin-I, helospectin-II (Parker, D. S. et al., *J. Biol. Chem.* 259:11751-11755 (1984)),and helodermin (Hoshino, M. et al., *FEBS Lett.* 178:233-239 (1984)). Recently, we discovered another peptide that increases cAMP and stimulated the release of amylase in dispersed acinar cells. This peptide was found in *Heloderma horridum* venom and was termed exendin-3 (Eng, J. et al., *J. Biol. Chem.* 265: 20259-20262 (1990). Exendin-3 shares homology with VIP, secretin, helospectin-I and -II, and helodermin. The venom of *Heloderma suspectum* was examined and another peptide was purified from it. This peptide called exendin-4 is an analogue of exendin-3 with an identical sequence except for substitutions in residues 2 and 3 from the amino terminus (Eng, J. et al.,*J. Biol. Chem.* 267:742-7405(1992)). Experiments were done to establish that the exendins could stimulate cAMP activity in dispersed pancreatic acinar cells, and a specific antagonist, exendin(9-39) amide, which can inhibit the effects of the exendins, was identified. (Raufman, J. P. et al., *J. Biol. Chem.* 266: 2897-2902 (1991 )) Experiments were performed to establish that GLP-1 could interact with possible exendin receptors in dispersed pancreatic acinar cells in vitro (Raufman, J. P. et al., *J. Biol. Chem.* 267:21432-21437 (1992)).

SUMMARY OF THE INVENTION

This invention encompasses pharmaceutical compositions containing exendin-3 or exendin-4, or any combination thereof, and methods for the treatment of diabetes mellitus and the prevention of hyperglycemia.

The compositions of the invention will normalize hyperglycemia through glucose-dependent, insulin-dependent and insulin-independent mechanisms. Therefore they will be useful as primary agents for the treatment of type II diabetes mellitus and as adjunctive agents for the treatment of type I diabetes mellitus. The invention specifically provides for exendin-4(1-39) as an insulinotropic agent.

The use of an effective amount of exendins as a treatment for diabetes mellitus has the advantage of being more potent than other insulinotropic peptides. The present invention is especially suited for the treatment of patients with diabetes, both type I and type II, in that the action of the peptide is dependent on the glucose concentration of the blood, and thus the risk of hypoglycemic side effects are greatly reduced over the risks in using current methods of treatment. Thus the use of insulinotropic peptides such as exendin-3 and exendin-4, has many advantages in the treatment of diabetes mellitus over current methods.

The present invention also provides for inhibitory agents derived from the exendins. In particular, exendin-4(9-39) as an inhibitor of exendin-4 and GLP-1 insulinotropic activity.

The present invention also provides for a method for treating diabetes mellitus in an individual, wherein said method comprises providing an amount of an insulinotropic composition sufficient to treat said diabetes; said composition containing an insulinotropic molecule; wherein said molecule is selected from the group consisting of:
- (a) a peptide having the amino acid sequence substantially identicle to the sequence of exendin-3 or exendin-4 or fragments thereof; and
- (b) a derivative of said peptide (a), wherein said derivative is selected from the group consisting of:
  - (1) a pharmaceutically acceptable acid addition salt of said peptide;
  - (2) a pharmaceutically acceptable carboxylate salt of said peptide;
  - (3) a pharmaceutically acceptable lower alkyl ester of said peptide; and,
  - (4) a pharmaceutically acceptable amide of said peptide wherein said pharmaceutically acceptable amide is selected from the group consisting of amide, lower alkyl amide and lower dialkyl amide; wherein said molecule has an insulinotropic activity which exceeds the insulinotropic activity of exendin-3 or exendin-4 or fragments thereof.

Thus the invention provides for the peptides or peptide fragments, made synthetically or purified from natural sources, which embody the biological activity of the exendins, or fragments thereof, as described by the present specification.

BRIEF DESCRIPTION OF THE DRAWINGS

FIG. 2a, Dog #1. FIG. 2b, Dog #2. FIG. 2c, Dog #3. Serial injections of GLP-1(7-36) amide alternating with exendin-4 into the left atrium via a chronically indwelling catheter. GLP-1(7-36) amide was given at time 0 (0.1 nmol) and at 40 min (1 nmol). Exendin-4 was given at 20 min (0.1 nmol) and at 60 min (1 nmol). In 2c, the rise and fall in the baseline insulin between time 0 and 60 min is unexplained.

DETAILED DESCRIPTION OF THE INVENTION

Figure 1:
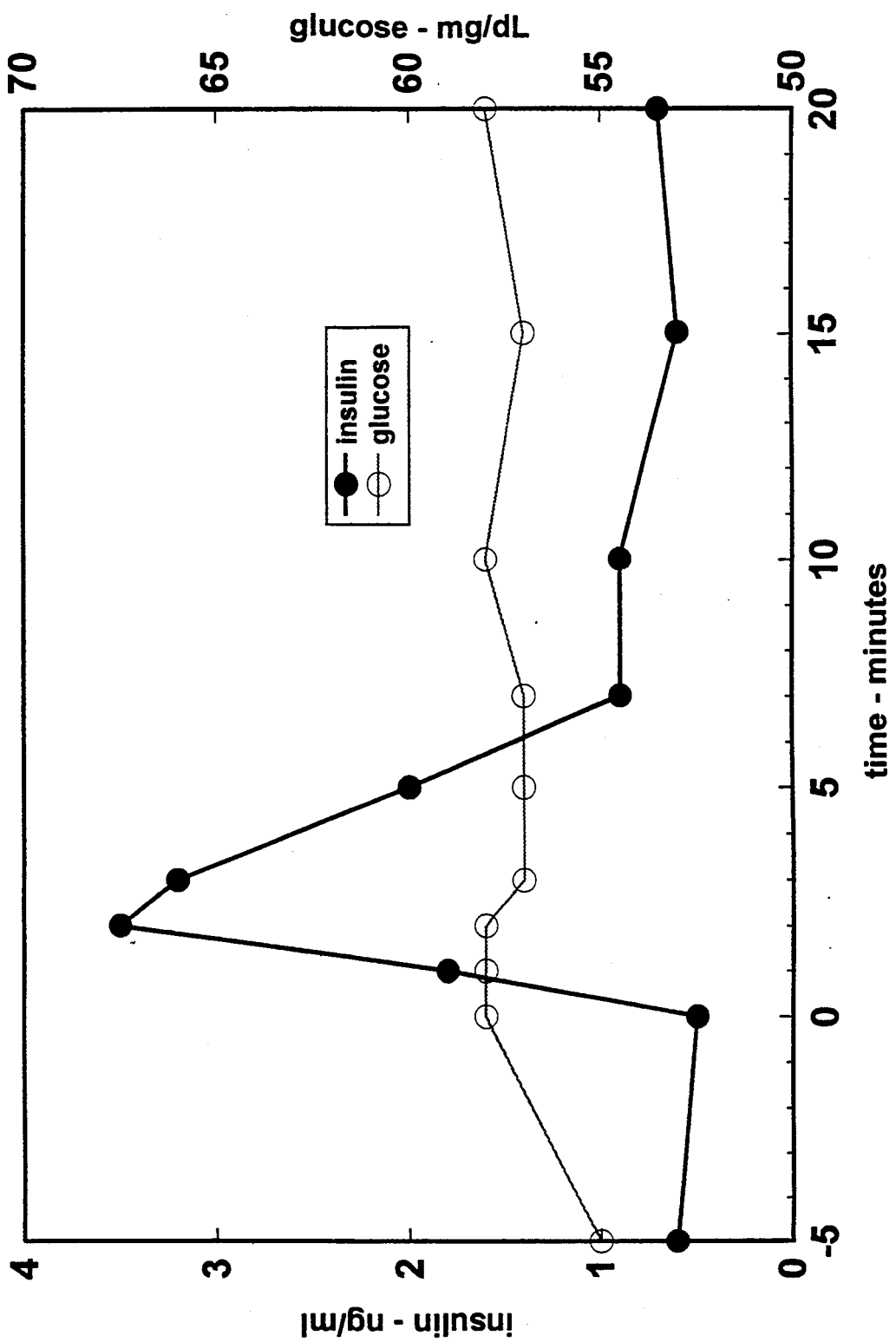
FIG. 1 is a graph showing exendin stimulated insulin secretion in a dog. Endogenous insulin secretion stimulated by exendin-3 (200 nmol) in a conscious dog. Exendin-3 was given as a bolus injection into a leg vain at time 0. Plasma was measured by radioimmunoassay.

The present invention provides for novel polypeptides which are unexpectedly useful as insulinotropic agents. Insulinotropic agents being agents which can stimulate, or cause the stimulation of, the synthesis or expression of the hormone insulin. The polypeptides of the present invention are termed exendin-3 and exendin-4. These peptides were originally isolated from the venom of *Heloderma horridum* and *Heloderma suspectum* respectively. In one embodiment of the invention, polypeptides corresponding to the amino acid sequence of exendin-3 and exendin-4 are synthesized by the solid phase method as previously described (Merrifield, J. M., *Chem. Soc.* 85: 2149 (1962); Stewart and Young, *Solid Phase Peptide Synthesis*, Freeman, San Francisco, 1969, pp. 27–66). In addition, it is also possible to isolate naturally occuring polypeptides from venom samples in a fashion similar to the original isolation of exendins 3 and 4. It is further possible to obtain the desired polypeptides by using recombinant DNA techniques (Maniatis, T. et al., *Molecular Biology: A Laboratory Manual*, Cold Spring Harbor, N.Y., 1982). The invention encompasses polypeptides which are insulinotropic and can be derived from naturally-occuring amino acid sequences. These proteins consist of the following amino acid sequences:

Exendin-3 [SEQ ID No:1] HSDGTFTSDL SKQMEEEAVR LFIEWLKNGG PSSGAPPPS

Exendin-4 [SEQ ID No:2] HGEGTFTSDL SKQMEEEAVR LFIEWLKNGG PSSGAPPPS

The invention also encompasses the insulinotropic fragments of exendin-4 comprising the amino acid sequentes:

Exendin-4(1-31) [SEQ ID No:3] HGEGTFTSDL SKQMEEAVR LFIEWLKNGG P $y^{31}$ Exendin-4(1-31) [SEQ ID No:4] HGEGTFTSDL SKQMEEEAVR LFIEWLKNGG Y The invention also encompasses the inhibitory fragment of exendin-4 comprising the amino acid sequence:

Exendin-4(9-39) [SEQ ID No:5] DL SKQMEEEAVR LFIEWLKNGG PSSGAPPPS

The invention further encompasses a method for the enhancement of insulin production or expression which comprises the steps of providing to a mammalian beta type pancreatic islet cell an effective amount of the insulinotropic peptides disclosed above.

Also provided for by the present invention are those amino acid sequences in the above peptides which are capable of functioning as insulinotropic hormones. In addition, the invention also provides for the addition of amino acids to enhance attachment to carrier molecules, or added to enhance the insulinotropic effect.

A material is said to be "substantially free of natural contaminants" if it has been substantially purified from materials with which it is normally and naturally found. Examples of natural contaminants of exendin-3 or exendin-4 are: other peptides, carbohydrates, glycosylated peptides, lipids, membrane, other venom components etc. A material is also said to be substantially free of natural contaminants if these contaminants are substantially absent of from a sample of the material.

The compounds of the present invention can be formulated according to known methods to prepare pharmaceutically useful compositions. In these compositions, exendin-3 and or exendin-4, or their functional derivatives are combined in admixture with a pharmaceutically acceptable carrier vehicle. Suitable vehicles and their formulations, inclusive of other human proteins, e.g. human serum albumin, are well known. In order to form an effective pharmaceutical composition, the composition will contain an effective amount of the exendin-3 or exendin-4, or functional derivatives together with a suitable amount of carrier vehicle. Other compositions may combine exendin-3 and exendin-4, or their functional derivatives with other effective drugs that may treat other symptoms, or the same symptoms.

The use of exendin-3 and 4 in compositions that may be injected intravenously, intramuscularly, subcutaneously, or intraperitoneally, would call for dosages of about 0.1 pg/kg to 1,000 mg/kg body weight depending on many individual factors such as age, severity of disease, total body weight, sex and other mitigating factors.

The insulinotropic properties of a compound may be determined by in vitro or in vivo assay. The compound in question may be administered to animals and monitoring the release of insulin. It is possible to monitor the increase in insulin production in cell culture as well.

The sequences of the invention also provide a means for identifying any specific mamalian analogs to the exendins. This can be accomplished by direct comparison of amino acid sequences, or by the translation of RNA or DNA sequences which may encode for the amino acid sequences of the invention, or by inhibition of activity by the specific exendin inhibitor, exendin (9-39) amide.

The sequences of the invention also provides a means for generating antibodies specific for the exendins, and further for the production of monoclonal antibodies for the exendins and fragments thereof. Thus the invention provides a means for purifying mammalian or other analogs to the exendins by the method of affinity chromatography.

Specific Examples

Testing was done to establish if exendin-3 or exendin-4 could stimulate pancreatic insulin secretion in mammals. Since both exendin-3 and exendin-4 peptides have about 50% homology with glucagon and GLP-1(7-36) (glucagon-like peptide-1), and GLP-1(7-36) was found to bind to exendin receptors, it was thought possible that exendins could act in similar fashion as GLP-1 on other receptors.

The examples which follow are illustrative of specific embodiments of the invention, and various uses thereof. They are set forth for explanatory purposes only, and are not to be taken as limiting the invention.

Example 1

The exendins are insulinotropins

Naural or synthetic exendin-3 and exendin-4 were tested in several biological systems, including conscious dog, anesthetized dog with chronic indwelling left atrial catheters, and beta TC-3 insulinoma cell line (described in D'Ambra et al., *Endocrinology* 126:2815-2822 (1990)) in cell culture. FIG. 1 shows an insulin secretory response to bolus injection of exendin-3 in a conscious dog with a seven-fold increase in insulin concentration above basal levels. Similar results are obtained using exendin-4. Since exendin-4 does not interact with VIP receptors and acts solely on exendin receptors, it has been used for subsequent studies.

Example 2

Exendin-4 insulin secretagogue activity is glucose dependent

Dogs with glucose concentrations clamped at graded levels show a glucose-dependent insulinotropic response to exendin-4. Dosages of exendin-4 which do not stimulate insulin release at fasting glucose concentrations of 50-75 mg/dL (such as 0.1 nmol exendin-4 given as a bolus) are able to produce a peak insulin response of one-fold above basal when given to dogs in a clamped, hyperglycemic state.

Exendin-4 stimulates a greater insulin secretory response than GLP-1

Figure 2A:
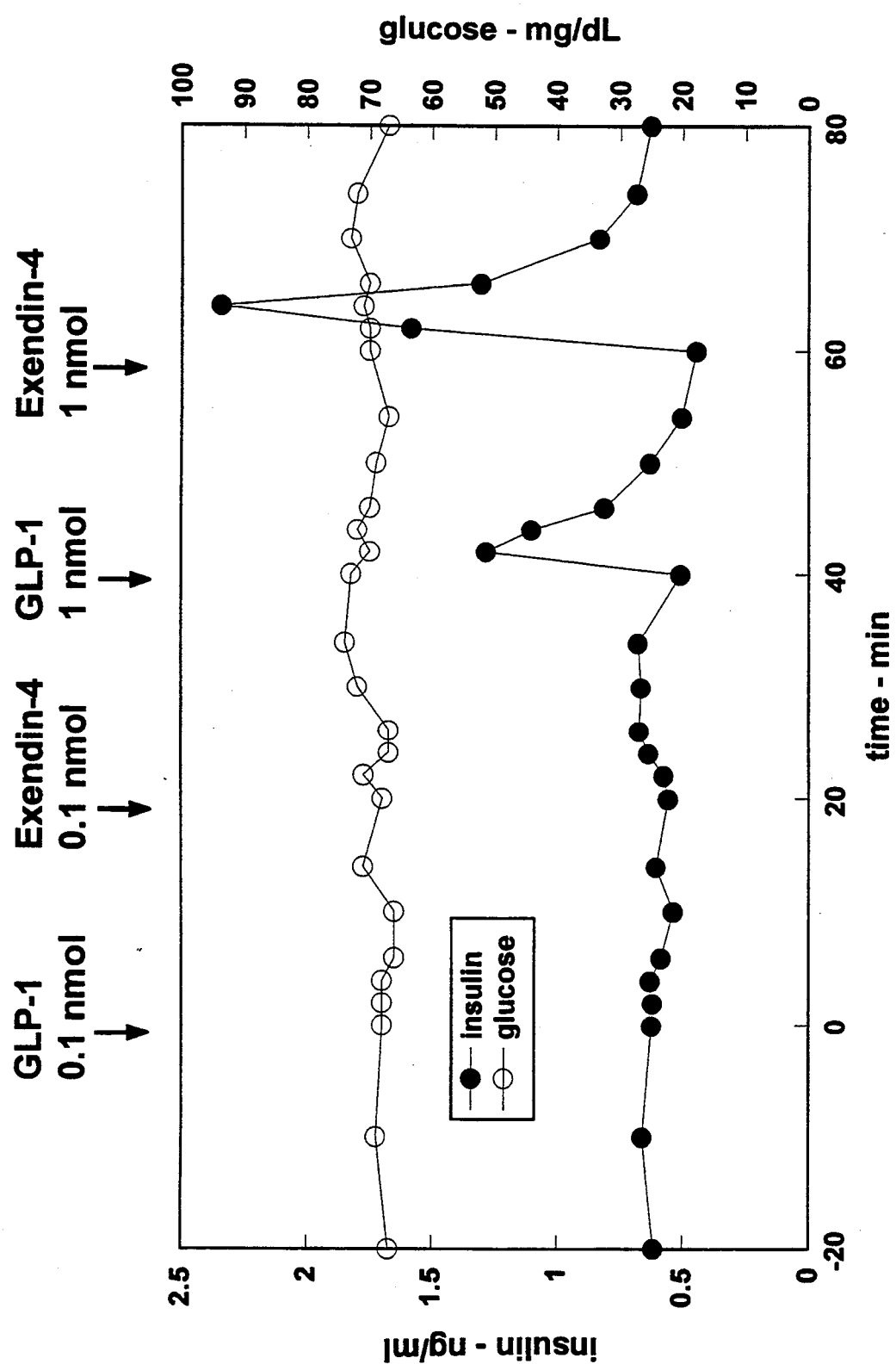
FIG. 2a & 2b & 2c are graphs showing the serial injection of GLP-1 and Exendin-4.
Figure 2B:
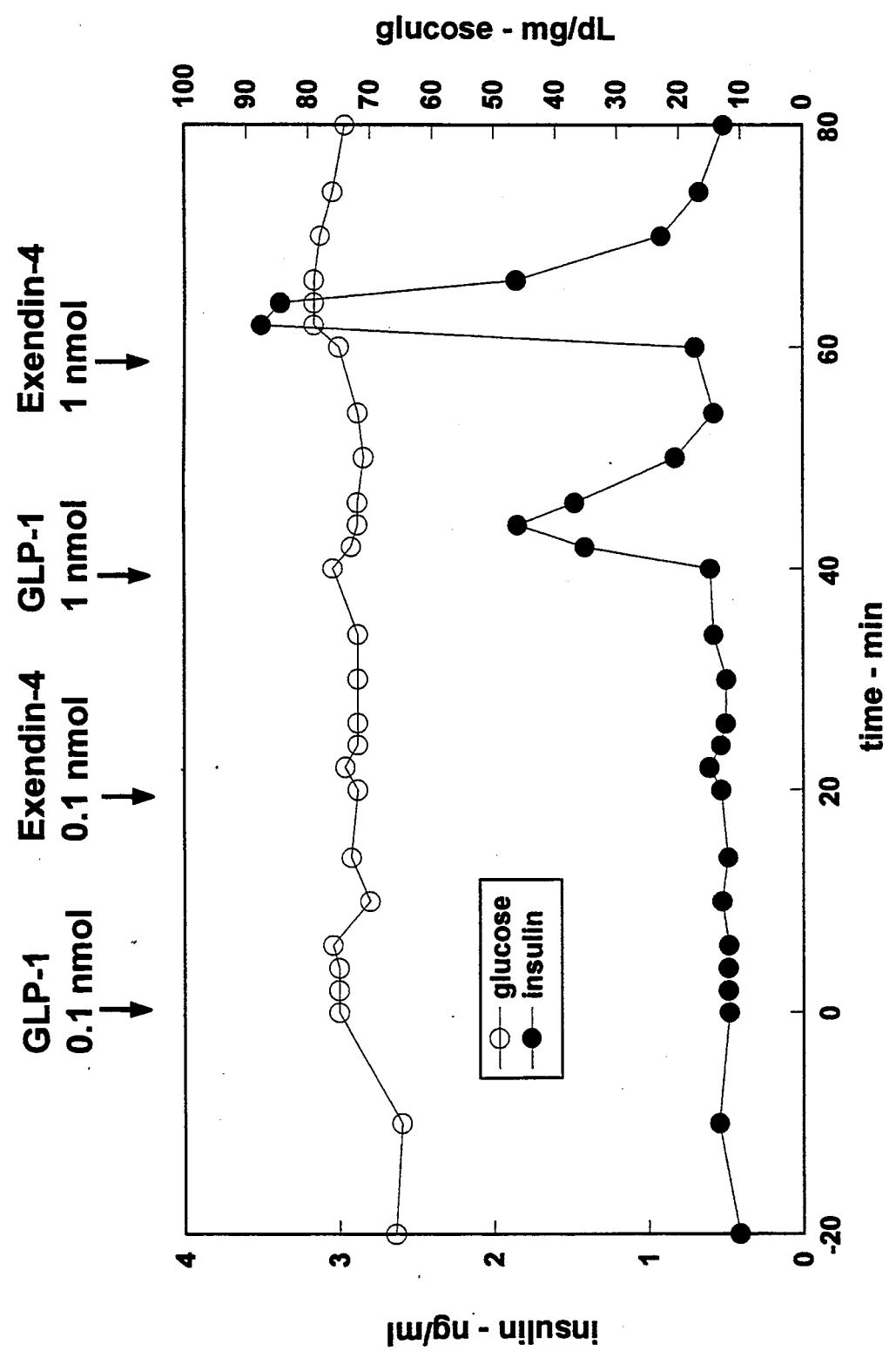
Figure 2C:
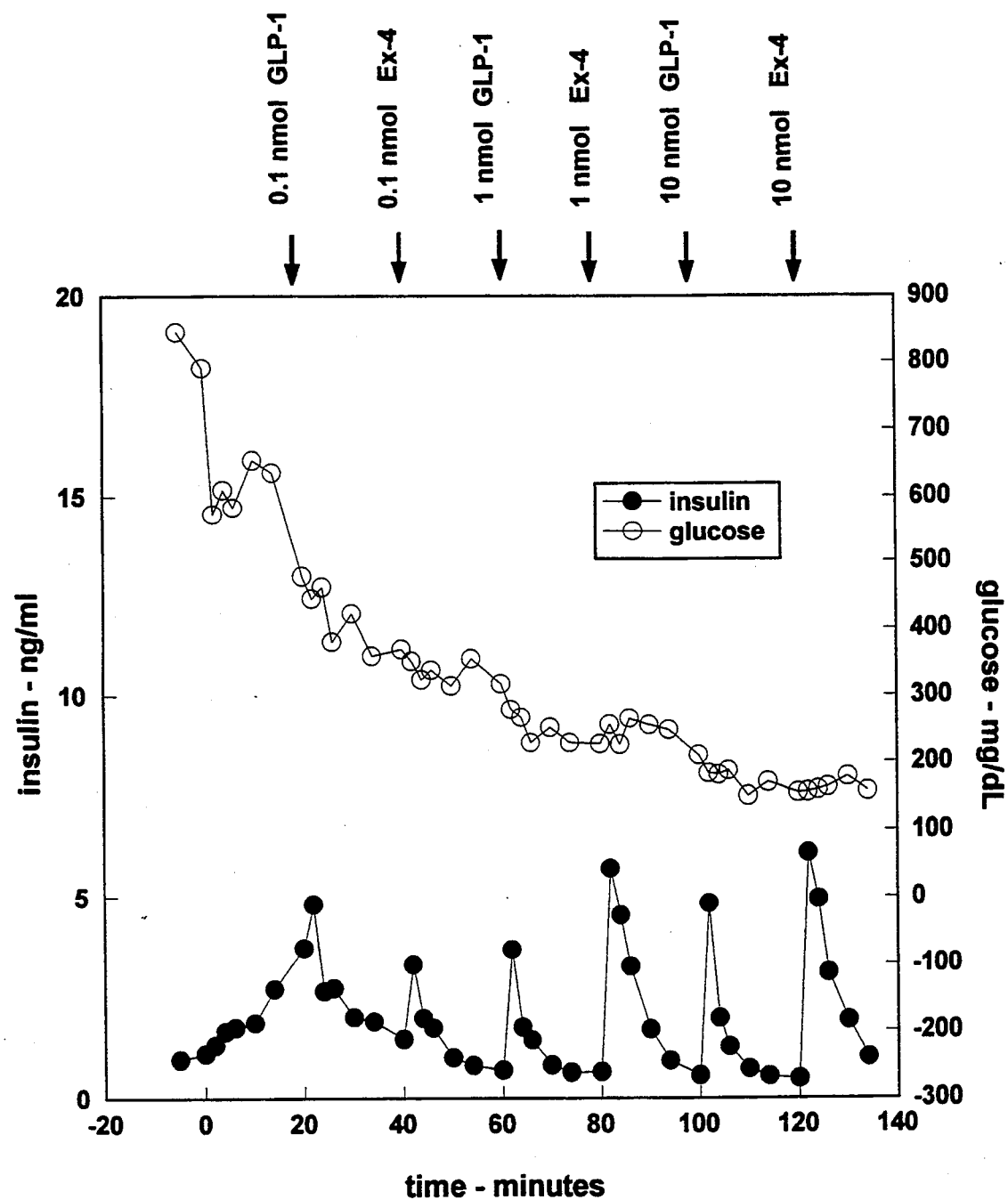

Synthetic exendin-4 was compared with GLP-1 (purchased from Peninsula Labs, Belmont, Calif.) by alternating injections of bolus doses into dogs with chronic indwelling left atrial catheters. Since GLP-1 and exendin-4 are glucose dependent in their insulinotropic response, paired equimolar doses of GLP-1 and exendin-4 were given with GLP-1 administered first to avoid the possibility that falling glucose levels in the animals cause a diminished insulinotropic response to GLP-1 relative to exendin-4. Dogs #1 and #2 in FIGS. 2a and 2b maintained constant fasting glucose concentrations throughout the experiments in a range between 60 and 80 mg/dL. FIGS. 2a, 2b and 2c show a comparison of insulinotropic responses to alternating bolus injections of GLP-1 and exendin-4 at 20 minute intervals and at increasing doses ranging from 0.1 nmol to 10 nmol ad-

TABLE 1

| Exendin-3 | HSDGTFTSDL | SKQMEEEAVR | LFIEWLKNGG | PSSGAPPPS |
| Exendin-4 | HGEGTFTSDL | SKQMEEEAVR | LFIEWLKNGG | PSSGAPPPS |
| GLP-1 | HAEGTFTSDV | SSYLEGOAAK | EFIAWLVKGR | |
| Glucagon | HSQGTFTSDY | SKYLDSRRAQ | DFVQWLMNT | |

Polypeptides corresponding to the amino acid sequence of exendin-3 and exendin-4 were synthesised by the solid phase method as previously described (Merrifield, J. M., *Chem. Soc.* 85:2149 (19625; Stewart and Young, *Solid Phase Peptide Synthesis*, Freeman, San Francisco, 1969, pp. 27-66). It is also possible to isolate naturally occuring polypeptides from venom samples in a fashion similar to the original isolation of exendins 3 and 4. It is further possible to obtain the desired polypeptides by using recombinant DNA techniques (Maniatis, T. et al., *Molecular Biology: A Laboratory Manual*, Cold Spring Harbor, N.Y., 19825).

ministered through chronic indwelling left atrial catheters into anesthetized dogs.

In contrast to the euglycemia present in the first two dogs, the third dog in FIG. 3c was exceptionally hyperglycemic, probably as a result of an infected catheter. Several points are illustrated by this experiment. First, euglycemic dogs normally do not respond to 0.1 nmol of either GLP-1 or exendin-4 with an insulin secretory resonse as illustrated by the first two dogs, whereas the hyperglycemic dog had clear insulinotropic responses to this lower dose of peptide. Second, the rapid normalization of hyperglycemia to euglycemic levels following modest doses of the two peptides reflects the great potential for use of these peptides in treatment of diabetic states. Third, despite the rapid normalization of the hyperglycemia, hypoglycemia does not occur. This class of therapeutic agents might be termed "euglycemic" agents. The potential for hypoglycemia caused by overdosages of these agents is minimized. Hypoglycemia is avoided even when the agents are given in the euglycemic state. Fourth, despite the administration of exendin-4 following an equivilent dose of GLP-1 in the setting of decreasing glucose levels, the insulin response as defined by area under the curve, is consistently 2-3 fold greater for exendin-4 compared to GLP-1. The greater response to exendin-4 holds true for the two euglycemic animals as well. A summary of the insulin responses is shown in Table 2.

TABLE 2

| Dog | Dose | AUC (GLP-1) | AUC (EX-4) | EX-4/GLP-1 |
| --- | --- | --- | --- | --- |
| #1 | 1 nmol | 2.0 | 4.1 | 2.1 |
| #2 | 1 nmol | 2.8 | 7.3 | 2.6 |
| #3 | 1 nmol | 5.0 | 12.9 | 2.6 |
|    | 10 nmol | 5.7 | 14.2 | 2.5 |

Table 2 shows the relative ratio of insulin secretion stimulated by serial injections of GLP-1 (7-36) amide and exendin-4 expressed as area under the curve (AUC). AUC=T-B where T=total insulin secreted (sum of concentrations at times 2,4,6, 10 mad 14 min. and B=baseline insulin=average of insulin concentrations at times 0 and 20 min. Multiplied by a factor of 5.

Example 3

Exendin(9-39) amide inhibits endogenous, exendin-4, and GLP-1 insulinotropic activity.

Figure 5:
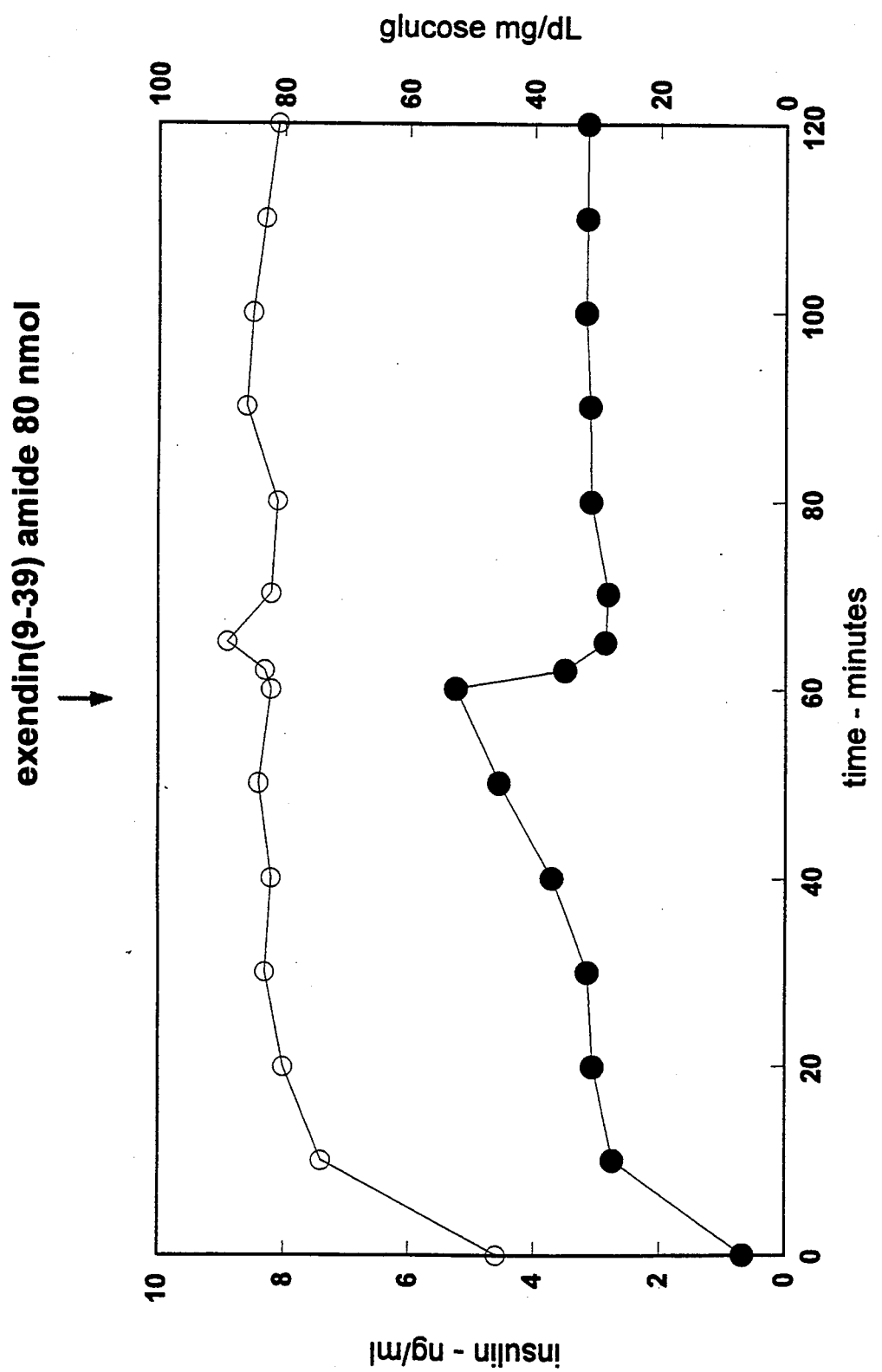
FIG. 5 is a graph demonstrating the effect of exendin antagonist on glucose -stimulated increase in insulin. Conscious dog infused with glucose at 200 mg/min beginning at time 0. A bolus injection of exendin(9-39) amide was made at 60 minutes.

Antagonistic peptides can arise by a number of mechanisms. The gene encoding the exendins may also encode for related peptides which have antagonistic activity. The production of antagonistic peptides may then be either initiated or suppressed by differential cleavage of the pre-propeptide. The antagonistic peptides may also arise through post-translational modification of the agonist peptide, specifically through differential cleavage to produce extended or truncated forms of the agonist peptide. In our studies of the structure-function relationship of exendin peptide sequences, the $NH_2$-terminally truncated exendin analog, exendin(9-39) amide, was shown to have potent antagonistic activity against exendin-3 and exendin-4 in a pancreatic acinar cell system measuring cAMP activity. (Raufman et al., *J. Biol. Chem.* 266:2897-2902 (1991); Eng et al., *J. Biol. Chem.* 267:7402-7505 (1992)). FIG. 5 shows the effect of exendin(9-39) amide when administered alone on circulating insulin levels while glucose levels are clamped at approximately 100% above fasting levels. Following injection of the antagonist there is a rapid decrease in circulating insulin levels to 60% of the maximum concentration. This result indicates that the antagonist inhibited an endogenous insulinotropin that accounted for a substantial portion of the insulin secretory response to hyperglycemia.

Figure 3:
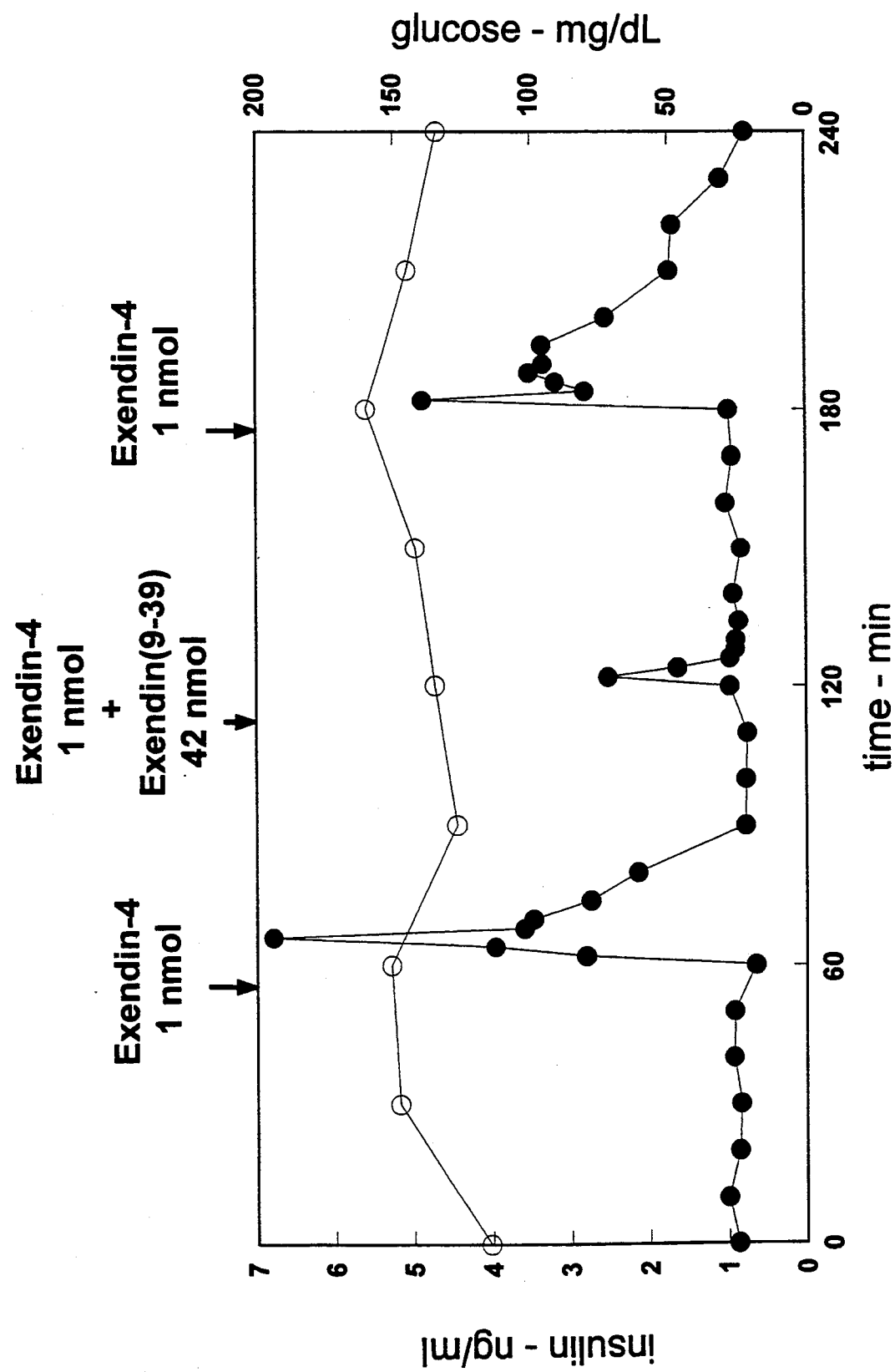
FIG. 3 is a graph illustrating the effect of exendin with and without antagonist. Insulin response in a normal dog to exendin-4 with or without exendin(9-39) amide. Glucose was infused at 100 mg/min. Exendin-4 (1 nmol) was given as an intravenous bolus at 60, 120 and 180 min. Exendin(9-39) amide, 42 nmol, was given together with exendin-4 at 120 min. The first phase of insulin release is greatly reduced and the second phase is abolished by this ratio of antagonist to agonist.

When exendin(9-39) amide is given together with exendin-4 at a molar ratio of 40:1, there is substantial inhibition of the insulin secretory response, as shown in FIG. 3. The second phase of insulin release is completely inhibited while the first phase is more resistant to complete inhibition. This finding suggests a differential sensitivity to inhibition between the first and second phases of insulin release. A pathological condition which may correlate to this phenomenon is a loss of first phase insulin secretion in type 2 diabetes.

Figure 7:
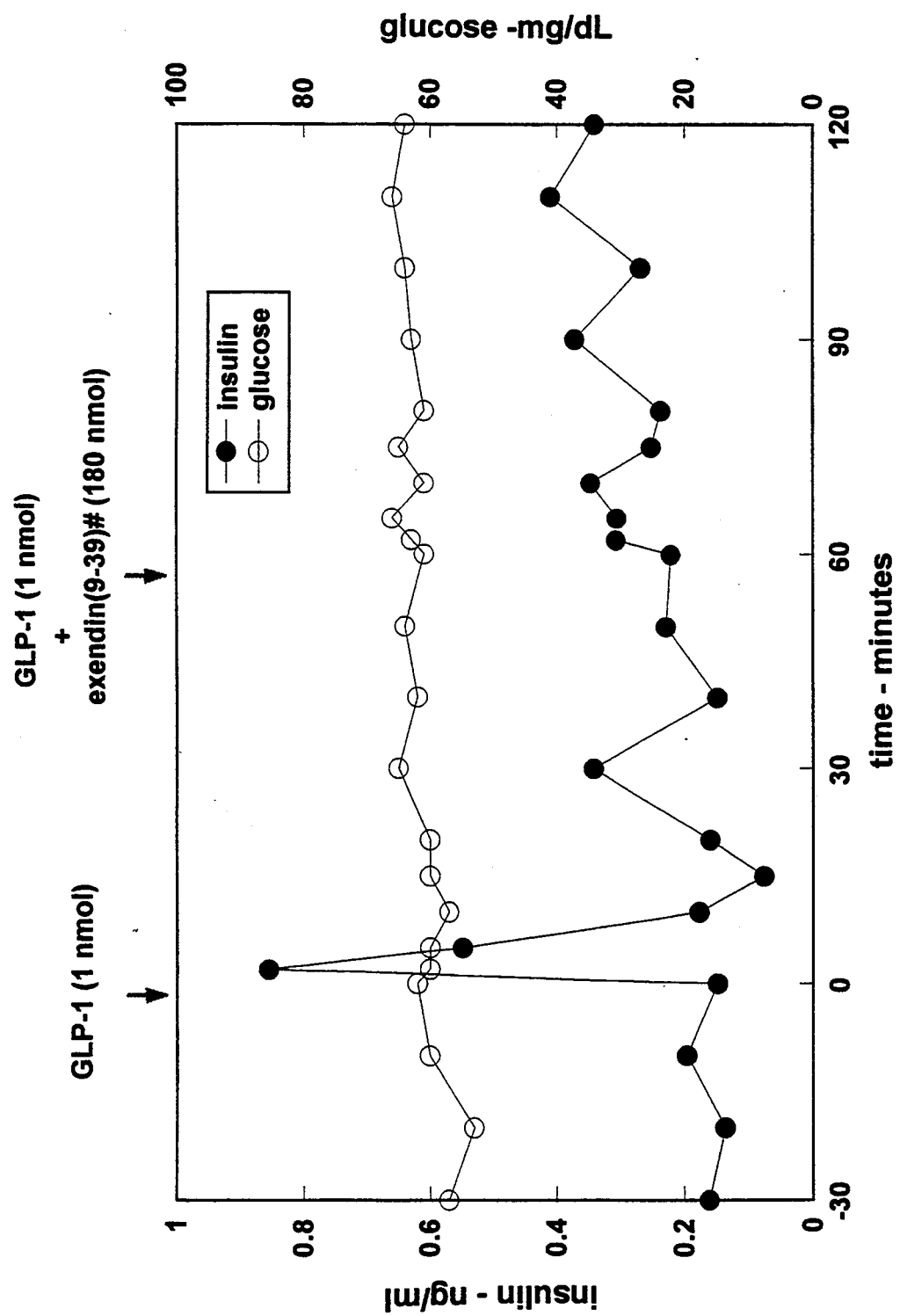
FIG. 7 is a graph illustrating the effect of GLP-1 with and without antagonist. Insulin responses in a fasted dog to GLP-1 (1 nmol) injected either alone at time 0 or together with exendin(9-39) amide (180 nmol) at time 60 min. GLP-1's insulinotropic activity is inhibited by exendin (9-39) amide.

When exendin(9-39) amide is given together with GLP-1 at molar ratio of 180:1 there is substantial inhibition of the insulin secretory response, as shown in FIG. 7.

Example 4

Exendin-4 acts directly on the beta cell

Figure 4:
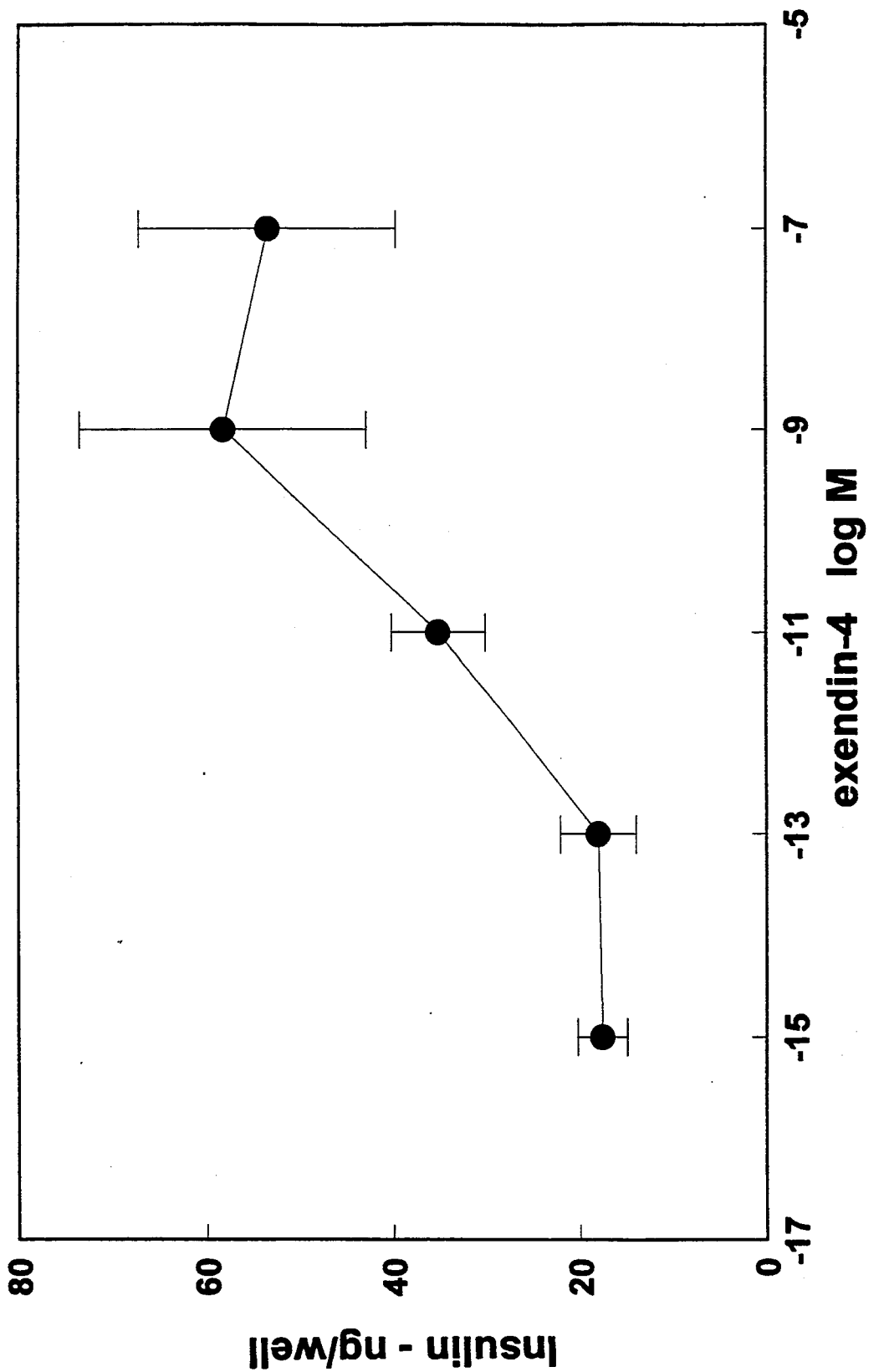
FIG. 4 is a graph illustrating the effect of exendin on cultured beta cells. βTC-3 cell insulin response to exendin-4, insulin mg/well vs. exendin-4 logM.

Beta TC-3 cells were obtained through Norman Fleischer (Diabetes Research and Training Center, Albert Einstein College of Medicine, N.Y.) and cultured in serum-containing media in 48-well culture dishes to confluency. Fresh media was added 24 hours before the cells were tested. The cells were tested in Earle's balanced salt solution containing IBMX, BSA and 16.7 mM glucose with graded concentrations of exendin-4 for 1 hour at 37° C. before collection of media supernate and assay for insulin concentrations. FIG. 4 shows a dose response curve to exendin-4 indicating that exendin-4 acts directly on beta cells to stimulate insulin secretion.

Example 5

Exendin-4 reduces the hyperglycemic state in a diabetic animal model

The db/db mouse is a genetically obese and diabetic strain of mouse. The db/db mouse develops hyperglycemia and hyperinsulinemia concomitant with its development of obesity and thus serves as a model of obese type 2 diabetes (NIDDM). Five 11-week old db/db mice purchased from The Jackson Laboratories (Bar Harbor, Me.) had sub-orbital sinus blood samples taken before and 60 minutes after intraperitoneal injection of exendin-4 at 10 nmol each animal (1 microgram/gram body weight). Blood glucose measurements were made with a glucose meter (YSI 1500 glucose analyzer, Yellow Springs, Ohio). The blood glucose levels in the animals were (average±standard error, in mg/dL glucose) 310±37 before and 181±37 one hour after administration of exendin-4. Thus, exendin-4 was able to reduce the diabetic levels of blood glucose by 40% in these animals.

Example 6

Figure 6:
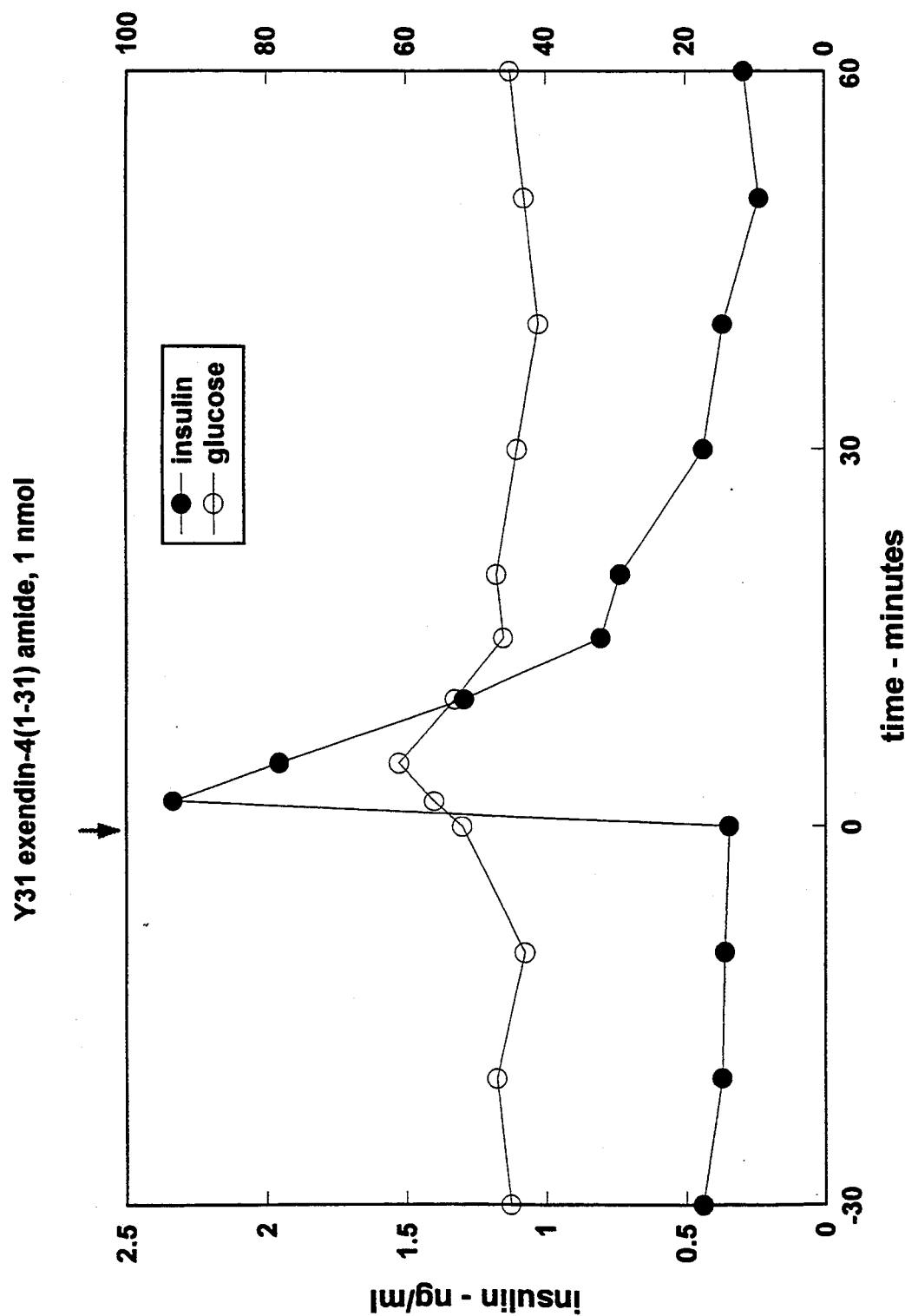
FIG. 6 is a graph illustrating the effect of Y31 exendin-4(1-31) amide. Conscious, fasted dog injected with a bolus of Y31 exendin-4(1-31) amide at time 0.

We have compared the effect of COOH-terminal truncations on the insulinotropic activity of exendin-4. The $Y^{31}$ mutation of exendin-4( 1-31) amide has a TYR for PRO substitution at position 31 from the amino terminus. This mutant was shown to have insulinotropic activity when infused into dog. FIG. 6 shows this result. This result indicates that the amino acids in the exendin-4 sequence located between residues 1 and 31 are important for the insulinotropic activity.

This invention thus provides for compounds that are an unexpectedly efficient means of stimulating insulin production in vitro and in vivo that will be useful for the treatment of diabetes mellitus, as well as specific inhibitors therof.

SEQUENCE LISTING

-continued ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
      ( A ) LENGTH: 39 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Peptide
      ( B ) LOCATION: 1..39
      ( D ) OTHER INFORMATION: /label=Exendin-3

( x i ) SEQUENCE DESCRIPTION: SEQ ID NO:1:

```
His Ser Asp Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
                20                  25                  30

Ser Gly Ala Pro Pro Pro Ser
            35
```

( 2 ) INFORMATION FOR SEQ ID NO:2:

( i ) SEQUENCE CHARACTERISTICS:
      ( A ) LENGTH: 39 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Peptide
      ( B ) LOCATION: 1..39
      ( D ) OTHER INFORMATION: /label=Exendin-4

( x i ) SEQUENCE DESCRIPTION: SEQ ID NO:2:

```
His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
                20                  25                  30

Ser Gly Ala Pro Pro Pro Ser
            35
```

( 2 ) INFORMATION FOR SEQ ID NO:3:

( i ) SEQUENCE CHARACTERISTICS:
      ( A ) LENGTH: 31 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Peptide
      ( B ) LOCATION: 1..31
      ( D ) OTHER INFORMATION: /label=Exendin-1-31
          / note="Exendin-4(1-31)"

( x i ) SEQUENCE DESCRIPTION: SEQ ID NO:3:

```
His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro
                20                  25                  30
```

( 2 ) INFORMATION FOR SEQ ID NO:4:

( i ) SEQUENCE CHARACTERISTICS:
      ( A ) LENGTH: 31 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Peptide
      ( B ) LOCATION: 1..31
      ( D ) OTHER INFORMATION: /label=Y31-Exendin4
             / note="Y-31-Exendin-4(1-31)"

( x i ) SEQUENCE DESCRIPTION: SEQ ID NO:4:

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Tyr
                20                  25                  30
```

( 2 ) INFORMATION FOR SEQ ID NO:5:

( i ) SEQUENCE CHARACTERISTICS:
      ( A ) LENGTH: 31 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Peptide
      ( B ) LOCATION: 1..31
      ( D ) OTHER INFORMATION: /label=Exendin-9-39
             / note="Exendin-4(9-39)"

( x i ) SEQUENCE DESCRIPTION: SEQ ID NO:5:

```
Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
                20                  25                  30
```

( 2 ) INFORMATION FOR SEQ ID NO:6:

( i ) SEQUENCE CHARACTERISTICS:
      ( A ) LENGTH: 30 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Peptide
      ( B ) LOCATION: 1..30
      ( D ) OTHER INFORMATION: /label=GLP-1-7-36
             / note="GLP-1(7-36) fragment"

( x i ) SEQUENCE DESCRIPTION: SEQ ID NO:6:

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
                20                  25                  30
```

( 2 ) INFORMATION FOR SEQ ID NO:7:

( i ) SEQUENCE CHARACTERISTICS:
      ( A ) LENGTH: 29 amino acids
      ( B ) TYPE: amino acid (C) STRANDEDNESS: single
(D) TOPOLOGY: linear (i i) MOLECULE TYPE: peptide (i x) FEATURE:
    (A) NAME/KEY: Peptide
    (B) LOCATION: 1..29
    (D) OTHER INFORMATION: /label=Glucagon (x i) SEQUENCE DESCRIPTION: SEQ ID NO:7:

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

What is claimed is:

1. A polypeptide having the amino acid sequence:
HGEGTFTSDL SKQMEEEAVR LFIEWLKNGG P[SEQ ID No:3].

2. A polypeptide having the amino acid sequence:
HGEGTFTSDL SKQMEEEAVR LFIEWLKNGG Y[SEQ ID No:4].

3. A pharmaceutical composition which comprises an effective insulinotropic amount of a substantially pure polypeptide, synthetic or purified from natural sources, having the amino acid sequence of claim 1 in a suitable carrier, which will stimulate the secretion of insulin in vivo.

4. A pharmaceutical composition which comprises an effective insulinotropic amount of a substantially pure polypeptide, synthetic or purified form natural sources, having the amino acid sequence of claim 2 in a suitable carrier, which will stimulate the secretion of insulin in vivo.

5. A method of stimulating insulin release in a mammal comprising administering an effective insulinotropic amount of a substantially pure polypeptide, synthetic or purified from natural sources, having the amino acid sequence:

HSDGTFITSDL SKQMEEEAVR
LFIEWLKNGG PSSGAPPPS (SEQ ID NO: 1), wherein the resulting insulinotropic effect is greater than that attainable by administration of GLP-1.

6. A method of stimulating insulin release in a mammal comprising administering an effective insulinotropic amount of a substantially pure polypeptide, synthetic or purified from natural sources, having the amino acid sequence:

HGEGTFTSDL SKQMEEEAVR
LFIEWLKNGG PSSGAPPPS (SEQ ID NO: 2), wherein the resulting insulinotropic effect is greater than that attainable by administration of GLP-1.

7. A method of inhibiting insulin release in a mammal comprising administering an effective amount of a substantially pure polypeptide, synthetic or purified from natural sources, having the amino acid sequence:

DL SKQMEEEAVR LFIEWLKNGG
PSSGAPPPS (SEQ ID NO: 5).

* * * * *

UNITED STATES PATENT AND TRADEMARK OFFICE
CERTIFICATE OF CORRECTION

| | |
|---|---|
| PATENT NO. | : 5,424,286 C1 |
| APPLICATION NO. | : 90/010653 |
| DATED | : January 11, 2011 |
| INVENTOR(S) | : John Eng |

It is certified that error appears in the above-identified patent and that said Letters Patent is hereby corrected as shown below:

On the cover of the patent:

Item "(73) Assignee: Eli Lilly and Company, Indianapolis, IN (US)" should be deleted.

Signed and Sealed this
Twenty-ninth Day of March, 2011

David J. Kappos
*Director of the United States Patent and Trademark Office*

US005424286C1

(12) EX PARTE REEXAMINATION CERTIFICATE (7970th)
United States Patent
Eng

(10) Number: US 5,424,286 C1
(45) Certificate Issued: Jan. 11, 2011

(54) EXENDIN-3 AND EXENDIN-4 POLYPEPTIDES, AND PHARMACEUTICAL COMPOSITIONS COMPRISING SAME

(75) Inventor: John Eng, Bronx, NY (US)

(73) Assignee: Eli Lilly and Company, Indianapolis, IN (US)

Reexamination Request:
No. 90/010,653, Aug. 21, 2009

Reexamination Certificate for:
Patent No.: 5,424,286
Issued: Jun. 13, 1995
Appl. No.: 08/066,480
Filed: May 24, 1993

(51) Int. Cl.
*A61K 38/00* (2006.01)
*C07K 14/435* (2006.01)
*C07K 14/575* (2006.01)

(52) U.S. Cl. ............................ 514/2; 514/866; 530/324; 435/69.1

(58) Field of Classification Search ........................ None
See application file for complete search history.

(56) References Cited

U.S. PATENT DOCUMENTS 4,761,287 A   8/1988   Geho
5,118,666 A   6/1992   Habener
5,120,712 A   6/1992   Habener

FOREIGN PATENT DOCUMENTS

WO   WO9111457 A1   8/1991
WO   WO9112800 A1   9/1991

OTHER PUBLICATIONS

Raufman JP, Singh L, Singh G, Eng J; "Truncated Glucagon–Like Peptide–1 [GLP–1(7–36)NH$_2$]Interacts with Exendin Receptors on Dispersed Acini from Guinea Pig and Rat Pancreas," Gastroenterology Apr.; 102(4):A751 1992.
Raufman JP, Singh L, Singh G, Eng J, "Truncated glucagon–like peptide–1 interacts with exendin receptors on dispersed acini from guinea pig pancreas. Identification of a mammalian analogue of the reptilian pepetide exendin–4," J Biol Chem. Oct. 25;267(30):21432–7 1992.
Eng J, Kleinman WA, Singh L, Singh G, Raufman JP, "Isolation and characterization of exendin–4, an exendin–3 analogue, from Heloderma suspectum venom. Further evidence for an exendin receptor on dispersed acini from guinea pig pancreas," J Biol Chem. Apr. 15;267(11):7402–5 1992.
FASTA Sequence Comparson of GLP–1 and Exendin–4, performed at "fasta.bioch.virginia.edu" which cites W.R. Pearson & D.J. Lipman PNAS 85:2444–8 1988.
Göke R, Fehmann HC, Göke B, "Glucagon–like peptide–1(7–36) amide is a new incretin/enterogastrone candidate," Eur J Clin Invest. Apr.;221(2):135–44 1991.
Gefel D, Hendrick GK, Mojsov S, Habener J, Weir GC, "Glucagon–like peptide–I analogs: effects on insulin secretion and adenosine 3', 5'–monophosphate formation," Endocrinology. Apr. 1990;126(4):2164–8 1990.

Gutniak M, Orskov C, Holst JJ; Ahrén B, Efendic S, "Antidiabetogenic effect of glucagon–like peptide–1 (7–36)amide in normal subjects and patients with diabetes mellitus," N Engl J Med. May 14;326(20):1316–22 1992.
Rabinovitch A, Blondel B, Murray T, Mintz DH, "Cyclic adenosine–3',5'–monophosphate stimulates islet B cell replication in neonatal rat pancreatic monoplayer cultures," J Clin Invest. Nov.;66(5): 1065–71 1980.
Fehmann HC, Göke R Göke B, Eissele R, Arnold R, "Helodermin and islet hormone release in isolated rat pancreas," Int J Pancreatol. May;8(4):289–303 1991.
Anthony Tu (Editor), Handbook of Natural Toxins, Part II, Chapter 23, pp. 755–776 "A Lizard Venom: Gila Monster" by Anthony T. Tu, 1991.
Buckley Dl, Lundquist P, "Analysis fo the Degradation of Insulinotropin [GLP–1(7–37)] in Human Plasma and Production of Degradation Resistant Analogs," 9th International Symposium on Gastrointestinal Hormones. Leuven, Belgium, Sep. 1–5, 1992. Abstracts, Regul Pept. Jul. 23;40(2):117 1992.
Nathan DM, Schreiber E, Fogel H, Mojsov S, Habener JF, "Insulinotropic action of glucagonlike peptide–I–(7–37) in diabetic and nondiabetic subjects," Diabetes Care. Feb.;15(2):270–6 1992.
Montague W, Howell SL, "The mode of action of adenosine 3':5'–cyclic monophosphate in mammalian islets of Langerhans. Effects of insulin secretagogues on islet–cell protein kinase activity," Biochem J. May;134(1):321–7 1973.
Raufman JP, Singh L, Eng J, "Use of Exendin(9–39)NH$_2$, A Specific Exendin Receptor Antagonist, to Detect the Interaction of Mammalian Peptides with Pancreatic Exendin Receptors," Gastroenterology, May; 100(5):A296 1991.
Raufman JP, Rai A, Eng J, "Truncated Glucagon–like Peptide–1 [GLP–1(7–36)NH$_2$] interacts with Exendin receptors on dispersed chief cells from guinea pig stomach," 9th International Symposium on Gastrointestinal Hormones, Leuven, Belgium, Sep. 1–5, 1992, Regul Pept. Jul. 23;40(2)234 1992.
Göke R, Eng J, Fehmann HC, Göke B, "Exendin–4 is a super–agonist and Exending(9–39)amide a potent antagonist at the Glucagon–like Peptide–1 receptor of insulinoma cells," Diabetes. May;42 Suppl 1:112A. American Diabetes Association. 53rd annual meeting. Jun. 12–15, 1993. Abstracts.
Singh G, Eng J, Raufman JP, "Characterization of Exendin Receptors on Dispersed Pancreatic Acini using $^{125}$I–[Y$^{39}$] Exendin–4," Gastroenterology, Apr.; 104(4):A337 1993.
Scheep W, Schmidtler J, Riedel Th, Raufmen JP, Eng J, Schusdziarra V, Classen M, "Exendin–4 and Glucagon–Like Peptide–1 (7–36)NH$_2$ Act on Identical Receptors on Rat Parietal Cells to Stimulate cAMP–Dependent H+–Production," Gastroenterology, Apr.; 104(4):A853 1993.

(Continued)

*Primary Examiner*—Padmashri Ponnaluri

(57) ABSTRACT

This invention encompasses pharmaceutical compositions containing exendin-3 or exendin-4, fragments thereof, or any combination thereof, and methods for the treatment of diabetes mellitus and the prevention of hyperglycemia.

OTHER PUBLICATIONS

Singh G, Rai A, Eng J, Raufman JP, "Use of $^{125}$I-[Y$^{39}$] Exendin–4 to Characterize Exendin/TGLP–1 Receptors on Gastric Chief Cells," Gastroenterology, Apr.; 104(4):A854 1993.

Suzuki S, Kawai K, Ohashi S, Watanabe Y, Yamashita K., "Comparison of the insulinotropic activity of glucagon–superfamily peptides in rat pancreas perfusion," Horm Metab Res. Oct.;24(10):458–61 1992.

Eng J, Eng C, "Exendin–3 and –4 are insulin secretagogues," Regulatory Peptides, vol. 40, p. 142 (Jul. 23) 1992.

Eng J, Andrews PC, Kleinman WA, Singh L, Raufman JP, "Purification and structure of exendin–3, a new pancreatic secretagogue isolated from Helodema horridum venom," J Biol Chem. Nov. 25;265(33):20259–62 1990.

Eng J, Kleinman W, Singh L, Raufman JP, "Isolation of Exendin–4, an analog of Exendin–3 from Helodema suspectum venom," 8th International Symposium on Gastrointestinal Hormones, Digestion, vol. 46 (Supplement 1), p. 29, Abstract 77 1990.

Raufman JP, Singh L, Eng J, "Exendin–3, a novel peptide from Heloderm horridum venom, interacts with vasoactive intestinal peptide receptors and a newly described receptor on dispersed acini from guinea pig pancreas. Description of exendin–3(9–39) amide, a specific exendin receptor antagonist," J Biol Chem. Feb.15;266(5):2897–902 1991.

FASTA Sequence Comparison of GLP–1 and Exendin–3, performed at "fasta.bioch.virginia.edu" which cites W.R. Pearson & D.J. Lipman PNAS 85:2444–8 1988.

FASTA Sequence Comparison of Exendin–3 and Exendin–4, performed at "fasta.bioch.virginia.edu" which cites W.R. Pearson & D.J. Lipman PNAS 85:2444–8 1988.

Göke R, Conlon JM, "Receptors for glucagon–like peptide–1(7–36) amide on rat insulinoma–derived cells," J Endocrinol. Mar.,116(3):357–62 1988.

Alberts B, Bray D, Lewis J, Raff, M, Roberts, K, Watson JD, Molecular Biology of the Cell, Second Edition, Chapter 3 "Macromolecules: Structure, Shape, and Information," pp. 117–118 1989.

Allen Journal of Experimental Medicine, 31(4):381–402 (1920).

Aliman, From Lizard Saliva to Diabetes Drug, Kidhaven Press, Thomson Gale, 2006.

BYETTA® Package Insert, pp. 1–26 (2009). See p. 11.

Charles et al, The Journal of Biological Chemistry, 250(15):6134–6140. (1975).

Eng et al, Peptides, 8:165–168 (1987).

Eng et al, Peptides, 11:683–685 (1990).

Eng, The Mount Sinai Journal of Medicine, 59(2):147–149 (Mar. 1992).

Goke et al, Journal of Molecular Endocrinology, 2:93–98 (1989).

Gray, Anatomy of the Human Body, 13th American Edition, pp. 1502–1514 (1985).

Gros et al, Endocrinology, 130:1263–1270 (1992).

Gros et al, Endocrinology, 133:631–638 (1993).

Guyton, Textbook of Medical Physiology, 4th Edition, p. 915 (1971).

Hellman et al, Proc. Natl. Acad. Sci. USA, 71(9):3405–3409 (1974).

Henderson et al, Gut, 22:158–167 (1981).

Homans, Journal of Medical Research, XXXIII(1):1–53 (1915).

Hoshino et al, FEBS Letters, 178(2):233–239 (1984).

Howell et al, Biochem. J. 136:343–349 (1973).

Huang et al, Horm. Metabol. Res., 19:542–544 (1987).

Kanse et al, FEBS Letters, 241 (1,2):209–212 (1988).

King et al, Endocrinology, 103(4):1321–1327 (1978).

Koenig et al, Proc. Nat. Acad. Sci. USA, 72(9):3687–3691 (1975).

Malhotra et al, Regulatory Peptides, 41:149–156 (1992).

Mattheeuws et al, Am. J. Vet. Res., 45(1):98–103 (1984).

Meyerovitch et al, J. Clin. Invest., 87:1286–1294(1991).

Morgan et al, Biochem. J., 226:571–576 (1985).

Naruse et al, Can. J. Physiol. Pharmcol., 64(Suppl):23, Abstract 150 (1986).

Nielsen et al, Regulatory Peptides, 117:77–88 (2004).

Nourse, The Body, Revised Edition, Time–Life Books Alexandria, VA, pp. 168–178 (1981).

Parker et al, J. Biol. Chem., 259(19):11751–11755 (1984).

Pearson et al, Proc. Natl, Acad. Sci. USA, 85:2444–2448 (1988).

Rai et al, Am. J. Physiol., 265:G118–G125 (1993).

Raufman et al, Am. J. Physiol., 242:G470–G474 (1982).

Richter et al, FEBS Letters, 280(2):247–250 (1991).

Samols et al, Diabetes, 15:855–866 (1966).

Shinomura et al, Regulatory Peptides, 23:299–308 (1988).

Unson et al, The Journal of Biological Chemistry, 264(2):789–794 (1989).

Unson et al, Proc. Natl. Acad. Sci. USA, 84:4083–4087 (1987).

Yu et al, Peptides, 10:1195–1197 (1989).

Yu et al, Proc. Natl. Acad. Sci. USA, 87:9766–9768 (1990).

Yu et al, Regulatory Peptides, 32:39–45 (1991).

Zheng et al, Endocrinology, 120:714–717 (1987).

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 5 and 6 is confirmed.

Claims 1-4 and 7 are cancelled.

New claims 8-14 are added and determined to be patentable.

*8. The method of claim 6, wherein the method of stimulating insulin release treats type II diabetes mellitus.*

*9. The method of claim 6, wherein the mammal is a human.*

*10. The method of claim 6, wherein the polypeptide is administered by subcutaneous injection.*

*11. The method of claim 6, wherein the substantially pure polypeptide is synthetic.*

*12. A method of treating type II diabetes mellitus by stimulating insulin release in a human comprising administering an effective insulinotropic amount of a substantially pure polypeptide, synthetic or purified from natural sources, having the amino acid sequence:*

HGEGTFTSDLSKQMEEEAVRLFIEWLKNGGPSSGAPPPS (SEQ ID No. 2),

*wherein the resulting insulinotropic effect is greater than that attainable by administration of GLP-1.*

*13. The method of claim 12, wherein the polypeptide is administered by subcutaneous injection.*

*14. The method of claim 12, wherein the substantially pure polypeptide is synthetic.*

\* \* \* \* \*